United States Patent [19]

Goldstein et al.

[11] 4,079,127

[45] Mar. 14, 1978

[54] THYMOSIN ALPHA 1

[75] Inventors: Allan L. Goldstein; Teresa L. K. Low, both of Galveston, Tex.; Chun-Yen Lai, Clifton; Su-Sun Wang, Bloomfield, both of N.J.

[73] Assignees: Board of Regents of the University of Texas; Hoffmann-La Roche, Inc., Nutley, N.J.

[21] Appl. No.: 766,638

[22] Filed: Feb. 8, 1977

Related U.S. Application Data

[63] Continuation-in-part of Ser. No. 736,638, Oct. 28, 1976, abandoned.

[51] Int. Cl.$^2$ .................... A61K 37/00; C07C 103/52
[52] U.S. Cl. ............................ 424/177; 260/112.5 R
[58] Field of Search ................. 260/112.5 R; 424/177

[56] References Cited

PUBLICATIONS

Goldstein, Nature 247, 1974, pp. 11–14.

Primary Examiner—Delbert R. Phillips
Attorney, Agent, or Firm—Samuel L. Welt; Jon S. Saxe; George M. Gould

[57] ABSTRACT

The amino acid sequence of a biologically active polypeptide hormone isolated from calf thymus termed thymosin $\alpha_1$ has been determined. Thymosin $\alpha_1$ is a heat stable acidic molecule composed of 28 amino acid residues. This peptide is one of several present in thymosin fraction 5 which participate in the regulation, differentiation and function of thymic dependent lymphocytes (T cells).

3 Claims, No Drawings

THYMOSIN ALPHA 1

The invention described herein was made in part in the course of work under a grant or award from the Department of Health, Education and Welfare.

RELATED APPLICATION

This application is a continuation-in-part of copending application Ser. No. 736,638, filed Oct. 28, 1976, now abandoned.

BACKGROUND OF THE INVENTION

The importance of the thymus gland in the development and senescence of immunological competence in animals and man is now generally accepted. Although there is little knowledge of the molecular events by which the thymus gland exerts control over T cell development, it appears that a vital part of the process occurs via a hormonal mechanism. The thymus produces a family of polypeptides termed thymosin and perhaps several other thymic hormones and/or factors which play an important role in the maturation, differentiation and function of T cells. Thymosin has been found to induce T cell differentiation and enhance immunological functions in genetically athymic mice, in adult thymectomized mice, in NZB mice with severe autoimmune reactions, in tumor bearing mice and in mice with casein-induced amyloidosis.

Thymosin fraction 5 is a potent immunopotentiating preparation and can act in lieu of the thymus gland to reconstitute immune functions in thymic deprived and/or immunodeprived individuals. Ongoing clinical trials with fraction 5 suggest that thymosin is effective in increasing T cell numbers and mormalizing immune function in children with thymic dependent primry immunodeficiency diseases and can increase T cell numbers in immnodepressed cancer patients.

Analytical polyacrylamide gel electrophoresis and isoelectric focusing have demonstrated that fraction 5 consists of 10-15 major components and 20 or more minor components with molecular weights ranging from 1,000 to 15,000.

DESCRIPTION OF THE INVENTION

The present invention relates to the isolation and first complete structural determination of an acidic polypeptide isolated from thymosin fraction 5. This peptide has been termed thymosin $\alpha_1$. Thymosin $\alpha_1$ has been found to be 10 to 1,000 times more active than fraction 5 in several in vitro and in vivo assay systems designed to measure T cell differentiation and function.

Thymosin $\alpha_1$ has a molecular weight of 3,108 and a pH in the range of 4.0-4.3 as determined by slab gel isoelectric focusing at a pH range of 3-5. The compound has the following amino acid sequence:

(N-acetyl)-Ser-Asp-Ala-Ala-Val$^5$-Asp-Thr-Ser-Ser-Glu$^{10}$-He-Thr-Thr-Lys-Asp$^{15}$-Leu-Lys-Glu-Lys-Lys$^{20}$-Glu-Val-Val-Glu-Glu$^{25}$-Ala-Glu-Asn-OH.

Thymosin $\alpha_1$ was isolated from fraction 5 by a combination of ion-exchange chromatography and gel filtration.

Lyophylized thymosin fraction 5 was chromatographed on a column of carboxymethyl-cellulose in 10 mM acetate buffer (Na), pH 5.0 containing 1.0 mM 2-mercaptoethanol. The column was washed first with the buffer followed by a linear gradient of 2 liters each of starting buffer and the same buffer containing 1.0 M NaCl. The first protein fraction was gel-filtered on a Sephadex G-25 column in sterile water. The second protein peak from the Sephadex column was applied on a DEAE-cellulose column (DE-32) equilibrated with 50 mM Tris, 1.0 mM 2-mercaptoethanol, pH 8.0. The column was eluted with the starting buffer followed by a gradient of 1.3 liters each of starting buffer and the same buffer containing 0.8 M NaCl. The first sixth of the protein peak from the DE-32 column was further purified by passing two times through a Sephadex G-75 column in 6.0 M guanidine-HCl, 10 mM Tris, pH 7.5. A single narrow cut was made from the protein pool and desalted on a Sephadex G-10 column in sterile water. The purified sample so obtained is identified as thymosin $\alpha_1$. The yield of thymosin $\alpha_1$ from fraction 5 is about 0.6%. The preparation is free of carbohydrate and nucleotide.

Gels containing 15% acrylamide were run under both basic (pH 8.3) and acidic (pH 2.9) conditions. Gels for isoelectric focusing were either purchased from LKB (PAG$_{plate}$, pH 3.5-9.5) or prepared by a modification of methods described by Awdeth et al., Nature 219, 66 (1968) and Wilson et al., Clinica Chemica Acta 49, 79 (1973).

Isoelectric focusing was conducted for 90 minutes using a constant power of 25 watts (LKB Model 2103 power supply). The gels were fixed in 15% TCA (w/v), 25% isopropanol for 16 hours and stained with 0.05% (w/v) Coomassie brilliant blue in 25% isopropanol, 10% acetic acid overnight. Destaining was carried out in 10% acetic acid.

Enzymatic digestion was performed in 0.05M Tris-HCl buffer, pH 8.0 or 1% ammonium bicarbonate at pH 8.3 for 2 to 3 hours at 37°. Trypsin, chymotrypsin, thermolysin or subtilisin were added to the protein solution for a final enzyme-substrate ratio of 1:100 (w/w).

Separation of enzymatic digest of thymosin $\alpha_1$ was performed largely by paper electrophoresis and/or chromatography. In a two-dimensional separation, paper chromatography was carried out first, with n-butanol: glacial acetic acid: water = 4:1:5 (v/v). This was followed by high-voltage electrophoresis at pH 1.9 for 30-40 minutes at 60 volts/cm. Peptides were detected by staining with cadmium-ninhydrin reagent or with fluorescamine in acetone. The amino acid sequences of the separated peptides were determined by the Edman degradation procedures and carboxypeptidase digestion methods. The presence of amide groups in a peptide was deduced from the latters mobility on high-voltage paper electrophoresis at pH 6.5.

For amino acid analysis, samples were hydrolyzed in 6N HCl in evacuated sealed tubes for 24-120 hours at 110°. Both Beckman/Spinco Model 119 (one-column system) and JEOL Model JLC-6AH (two-column system) amino acid analyzers were used.

Amino acid analyses were performed on 24, 48, 72 and 120 hour acid hydrolysates of thymosin $\alpha_1$. Table 1 shows the assumed number of residues per molecule based on these analyses. The number of residues based upon sequence analysis is also given in this table. The presence of small amounts of proline, glycine and methionine in the acid hydrolysates are atrributed to minor contaminants in the preparation. However, the quantity of contaminants were too small to interfere with sequence analysis. Thymosin $\alpha_1$ has a high aspartic and glutamic acid content and does not contain histidine, arginine, proline, glycine, cystine, methionine, tyrosine, phenylalanine or tryptophan residues.

assay measuring MIF production, and an in vitro human E-rosette assay.

Table 1

| Amino acid composition of thymosin $\alpha_1$ | | |
|---|---|---|
| Amino acid | Number of residues from acid hydrolysates* | Number of residues from the sequence+ |
| Lysine | 3.75 | 4 |
| Histidine | 0.04 | 0 |
| Arginine | 0.25 | 0 |
| Aspartic acid | 4.38 | 4 |
| Threonine+ | 2.75 | 3 |
| Serine+ | 2.81 | 3 |
| Glutamic acid | 6.44 | 6 |
| Proline | 0.50 | 0 |
| Glycine | 0.62 | 0 |
| Alanine | 3.44 | 3 |
| Half-cystine** | 0.00 | 0 |
| Valine*** | 3.25 | 3 |
| Methionine | 0.38 | 0 |
| Isoleucine*** | 1.13 | 1 |
| Leucine*** | 1.25 | 1 |
| Tyrosine | 0.11 | 0 |
| Phenylalanine | 0.12 | 0 |
| Tryptophan ‖ | 0.00 | 0 |

Footnotes, Table 1:
*The data are presented as numbers of residues per molecule. The molecule weight was assumed as 3,500. All values were the average of 4 determinations except that for Thr, Ser, Val, Ile and Leu.
+Aspartic acid and glutamic acid values are the sum of their acids and amides.
+Values were obtained by extraporation to zero time of hydrolysis;
**Determined as cysteic acid on performic acid oxidized sample.
***Values from the 120 hour hydrolysis.
‖ Determined by hydrolysis with 4M mercaptoethanesulfonic acid

Table 2

| Thymosin Activity in Various Bioassays | | | | |
|---|---|---|---|---|
| | MLR | MIF | E-Rosette | Mitogen* |
| Thymosin Fraction 5 (μg) | 1–10 | 1–5 | 1–10 | 1–10 |
| Thymosin $\alpha_1$ (μg) | N.A.+ | .01–.1 | .001–.01 | .01–.1 |

Footnote, Table 2
*In vivo 14 daily injections
+Not Active

Thymosin $\alpha_1$ did not react either with dansyl chloride or phenylisothiocyanate to yield the corresponding α-amino derivative of amino acids suggesting that its $NH_2$-terminus was blocked. The COOH-terminal sequence was determined as -Ala-Asn(OH) using the carboxy-peptidase method. Digestion of thymosin $\alpha_1$ with trypsin, chymotrypsin or thermolysin produced several peptides which provided information on the overlaps. Tables 3 and 4 list the amino acid composition of these peptides.

Table 3

| Amino acid composition* and N-terminal residue of tryptic peptides from thymosin $\alpha_1$ | | | | | | | |
|---|---|---|---|---|---|---|---|
| Amino acid | T1 | T3 | T4 | T5 | T5S1*** | T5A5# | T6 |
| Lysine | 1.94(2) | 0.90(1) | | 1.20(1) | | 1.0 | 0.92(1) |
| Aspartic acid | | | 1.02(1) | 2.04(2) | 1.19(1) | 1.23(1) | 0.97(1) |
| Threonine | | | | 2.62(3) | | 2.96(3) | |
| Serine | | | | 2.53(3) | 0.90(1) | 1.96(2) | |
| Glutamic acid | 1.06(1) | 1.03(1) | 3.84(4) | 1.09(1) | 0.15(0) | 1.56(1) | |
| Alanine | | | 1.01(1) | 2.10(2) | 1.91(2) | 1.11(1) | |
| Valine | | | 2.12(2) | 0.94(1) | | 0.86(1) | |
| Isoleucine | | | | 0.87(1) | | 1.0(1) | |
| Leucine | | | | | | | 1.11(1) |
| Total | 3 | 2 | 8 | 14 | 4 | 11 | 3 |
| N-Terminal+ | Glu | Glu | Glu | Blocked | Blocked | Ala | Asp |
| Charge at pH 6.5+ + | +1 | Neutral | −4 | ND** | ND | ND | Neutral |

Footnotes, Table 3:
*Results from hydrolysis in 6N HCl at 110° for 24 hours
+Determined by dansylation
++Determined by electrophoretic mobilities of high-voltage paper electrophoresis at pH 6.5 by the method of Offord Nature 211, 591 (1966)
**Not determined
***A peptide from subtilisin digest of T5. Isolated from ion-exchange column AG 50W-X2 in $H_2O$
A peptide from α-protease digest of T5, Isolated by high voltage paper electrophoresis.

Table 4

| Amino acid composition* and N-terminal residue of thermolysin and chymotryptic peptides of thymosin $\alpha_1$ | | | | | | | | |
|---|---|---|---|---|---|---|---|---|
| | Thermolysin peptides | | | | | Chymotryptic peptides | | |
| Amino acids | Th1 | Th2 | Th3 | Th4 | Th5 | C1 | C1Th1 | C2 |
| Lysine | 2.94(3) | 1.04(1) | | | | 0.90(1) | 0.91(1) | 2.71(3) |
| Aspartic acid | | 1.06(1) | 1.07(1) | 1.03(1) | | 1.97(2) | | 1.84(2) |
| Threonine | | | 0.99(1) | | | 2.65(3) | 1.71(2) | |
| Serine | | | 1.77(2) | | | 2.51(3) | | |
| Glutamic acid | 1.95(2) | | 1.13(1) | | 3.25(3) | 1.09(1) | | 5.58(5) |
| Alanine | | | | 1.04(1) | 1.00(1) | 1.95(2) | | 1.15(1) |
| Valine | | | | 1.68(2) | | 1.08(1) | | 1.73(2) |
| Isoleucine | | 0.95(1) | 1.04(1) | | | 1.05(1) | 1.03(1) | |
| Leucine | 1.00(1) | | | | | | | 0.82(1) |
| Total | 6 | 5 | 6 | 7 | 1 | 14 | 4 | 14 |
| N-Terminal+ | Leu | Ile | Val | Val | Ala | Blocked | Ile | Asp |
| Charge at pH 6.5+ + | +1 | Neutral | −2 | −3 | Neutral | ND** | +1 | ND |

Footnotes, Table 4:
*Results from hydrolysis in 6 N HCl at 110° for 24 hours
+Determined by dansylation
++Determined by electrophoretic mobilities of high-voltage paper electrophoresis at pH 6.5
**Not determined.

1.95(2)

As can be seen in Table 2, thymosin $\alpha_1$ is from 10 to 1,000 times more active than thymosin fraction 5 in an in vivo mouse mitogen assay, an in vitro lymphokine Trypic peptide T5 is assigned to the $NH_2$-terminal end of thymosin $\alpha_1$ for its lack of an α-amino group. A subtilisin digest of T5 was applied onto a cation exchange column packed with Bio-Rad AG 50W-X2 in $H_2O$. The column was washed with water and effluents assayed with fluorescamine. The peptide eluted with $H_2O$ was found to be a terpeptide (T5S1) with a blocked $NH_2$-terminus. When this peptide was hydrolyzed in 0.03 M HCl at 110° for 16 hrs., serine, aspartic acid, and a dipeptide Ala-Ala were released. Carboxypeptidase digestion of T5S1 released alanine. The amino acid sequence of the peptide was therefore, X-Ser-Asx-Ala-Ala. This was confirmed by the mass spectrometric analysis of T5S1. A Hitachi Perkin-Elmer RMU-6L mass spectrometer was used. As observed in the mass spectrum, the NH$_2$-terminus of this peptide was blocked by an acetyl group. From electrophoratic mobilities of Asp or Asn containing synthetic preparations the second residue was determined to be Asp.

T4 was the only tryptic peptide that did not contain a lysyl residue and its COOH-terminal sequence corresponded to that of the whole molecule. Thermolysin peptides Th1 and Th2 provided good overlap to order the other tryptic peptides. It was rather unexpected to find that chymotrypsin cleaved in the middle of the molecule at Lys-14 instead of Leu-16, thus suggesting a conformational susceptibility at this position.

The complete amino acid sequence of thymosin $\alpha_1$ has been given above. The information leading to the elucidation of the primary structure of this peptide hormone is summarized in Table 5.

The observation that thymosin $\alpha_1$ is more active than fraction 5 in enhancing some T cell assays (E-rosettes, lymphokine, mitogen), but not others such as the mixed lymphocyte response (MLR), suggests that more than one peptide component may be necessary to elicit full immunologic responsivity. Alternatively, a purification procedure such as the guanidine chromatography step may have altered the conformation of the molecule so as to permit its activity in the MLR assay. It may also be possible that trace amounts of guanidine hydrochloride in the preparation interferes with the bioassay.

Thymosin $\alpha_1$ may be administered to warm blooded mammals by parenteral application either intravenously, subcutaneously or intramuscularly. The compound is a potent immunopotentiating agent with a daily dosage in the range of about 1 to 100 μg/kg of body weight per day for intravenous administration. Obviously the required dosage will vary with the particular condition being treated, the severity of the condition and the duration of the treatment. A suitable dosage form for pharmaceutical use is 1 mg. of lyophilized thymosin $\alpha_1$ per vial to be reconstituted prior to use by the addition of sterile water or saline.

Table 5

Ac-Ser-Asp-Ala-Ala-Val-Asp-Thr-Ser-Ser-Glu-Ile-Thr-Thr-Lys-Asp-Leu-Lys-Glu-Lys-Lys-Glu-Val-Val-Glu-Glu-Ala-Glu-Asn

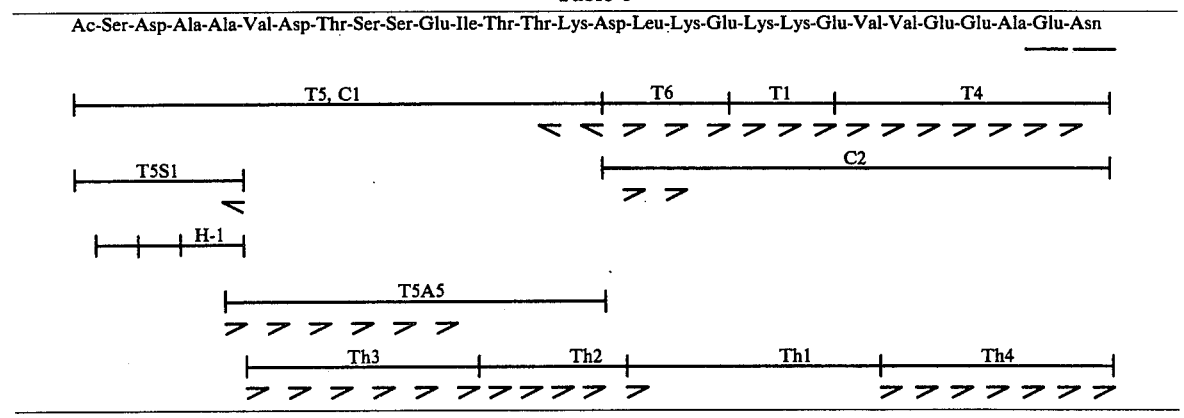

Table 5 is a diagram of the sequence analyses that have led to the elucidation of the primary structure of thymosin $\alpha_1$. Line segments denote the peptides isolated after digestion of thymosin $\alpha_1$ with trypsin (T1, etc.), chymotrypsin (C1 etc.), and thermolysin (Th1, etc.), and those from peptide T5 on digestion with subtilisin (T5S1) and α-protease (T5A5). Dilute acid hydrolysis of T5S1 (see text) produced free serine, aspartic acid and dipeptide Ala-Ala (H-1). Arrows pointing to right indicate residues degraded sequentially by Edman's method, and those pointing to left denote the sequence elucidated by carboxypeptidase digestion.

Comparison of the sequence of thymosin $\alpha_1$ with the known sequence of another thymic factor termed thymopoietin and a molecule termed ubiquitin reveals no homology.

Other thymic hormones that have been reported include THF and TF. The amino acid composition, but not the sequence has been described for THF. It appears that thymosin $\alpha_1$ and THF, although of similar molecular weight, differ greatly in amino acid composition. There is very little known about the chemistry of TF other than it is a small molecule (m.w. < 1000) and is heat labile. However, a comparison of their pI values in which TF has a value of 7.5 and thymosin $\alpha_1$ of 4–4.3, would suggest that they are different components.

Also included within the scope of the present invention are the pharmaceutically acceptable salts of thymosin $\alpha_1$ such as sodium or potassium or with strong organic bases such as guanidine. In addition, the counter ions of these cations as well as of lysine residues in thymosin $\alpha_1$, such as the hydrochloride, hydrobromide sulfate, phosphate, maleate, acetate, citrate, benzoate, succinate, malate, ascorbate and the like, may be included in the preparation.

We claim:

1. Thymosin $\alpha_1$ being a polypeptide essentially free of other thymic polypeptides and having the following amino acid sequence:

(N-acetyl)-Ser-Asp-Ala-Ala-Val$^5$-Asp-Thr-Ser-Ser-Glu$^{10}$-He-Thr-Thr-Lys-Asp$^{15}$-Leu-Lys-Glu-Lys-Lys$^{20}$-Glu-Val-Val-Glu-Glu$^{25}$-Ala-Glu-Asn-OH and the pharmaceutically acceptable acid addition salts or base salts thereof.

2. A method for reconstituting immune functions in thymic deprived or immunodeprived warm blooded mammals which method comprises administering to said mammal an immunopotentiating effective amount of thymosin $\alpha_1$.

3. The method of claim 2 wherein a daily dosage in the range of from about 1 to 100 μg/kg of body weight per day is administered.

* * * * *

UNITED STATES PATENT AND TRADEMARK OFFICE
CERTIFICATE OF CORRECTION

PATENT NO. : 4,079,127
DATED : March 14, 1978
INVENTOR(S) : Allan L. Goldstein; Teresa L.K. Low; Chun-Yen Lai; Su-Sun Wang It is certified that error appears in the above-identified patent and that said Letters Patent are hereby corrected as shown below:

Column 1, Line 53, "pH" should be: pI

Column 1, Line 57, "He" should be: Ile

Column 6, Line 55, "He" should be: Ile

Signed and Sealed this

Twenty-seventh Day of June 1978

[SEAL]

Attest:

RUTH C. MASON
Attesting Officer

DONALD W. BANNER
Commissioner of Patents and Trademarks